(12) United States Patent
Koch

(10) Patent No.: US 9,376,428 B2
(45) Date of Patent: Jun. 28, 2016

(54) METHODS FOR PRODUCING ORGANIC LIGHT EMITTING DIODE (OLED) MATERIALS

(71) Applicant: LOMOX LIMITED, Abercynon (GB)

(72) Inventor: Gene Carl Koch, Bishop Auckland (GB)

(73) Assignee: Lomox Limited, Congleton, Cheshire (GB)

( * ) Notice: Subject to any disclaimer, the term of this patent is extended or adjusted under 35 U.S.C. 154(b) by 0 days.

(21) Appl. No.: 14/399,285

(22) PCT Filed: May 9, 2013

(86) PCT No.: PCT/GB2013/000208
§ 371 (c)(1),
(2) Date: Nov. 6, 2014

(87) PCT Pub. No.: WO2013/167863
PCT Pub. Date: Nov. 14, 2013

(65) Prior Publication Data
US 2015/0141656 A1    May 21, 2015

(30) Foreign Application Priority Data

May 10, 2012 (GB) .................................. 1208136.0

(51) Int. Cl.
| | |
|---|---|
| *C07D 417/08* | (2006.01) |
| *H01L 51/00* | (2006.01) |
| *H01L 51/50* | (2006.01) |
| *C07C 1/34* | (2006.01) |
| *C07C 1/207* | (2006.01) |
| *C07C 5/03* | (2006.01) |
| *C07C 45/56* | (2006.01) |
| *C07C 45/68* | (2006.01) |
| *C07C 57/50* | (2006.01) |
| *C07C 69/616* | (2006.01) |
| *C07D 277/64* | (2006.01) |
| *C07F 7/08* | (2006.01) |
| *C09K 11/06* | (2006.01) |

(52) U.S. Cl.
CPC .......... *C07D 417/08* (2013.01); *H01L 51/0071* (2013.01); *C07C 1/2076* (2013.01); *C07C 1/34* (2013.01); *C07C 5/03* (2013.01); *C07C 45/56* (2013.01); *C07C 45/68* (2013.01); *C07C 57/50* (2013.01); *C07C 69/616* (2013.01); *C07C 2101/08* (2013.01); *C07C 2102/44* (2013.01); *C07C 2102/50* (2013.01); *C07C 2103/18* (2013.01); *C07C 2103/78* (2013.01); *C07C 2103/94* (2013.01); *C07D 277/64* (2013.01); *C07F 7/0827* (2013.01); *C09K 11/06* (2013.01); *C09K 2211/1011* (2013.01); *C09K 2211/1018* (2013.01); *H01L 51/0052* (2013.01); *H01L 51/0058* (2013.01); *H01L 51/50* (2013.01); *H01L 51/5012* (2013.01)

(58) Field of Classification Search
CPC ...................................................... C07D 417/08
See application file for complete search history.

(56) References Cited

FOREIGN PATENT DOCUMENTS

| | | |
|---|---|---|
| EP | 1215192 A2 | 6/2002 |
| JP | 3013952 A | 1/1991 |
| WO | WO-2009087364 A1 | 7/2009 |
| WO | WO-2010061896 A1 | 6/2010 |
| WO | WO-2011039506 A1 | 4/2011 |
| WO | WO-2013167857 A1 | 11/2013 |

OTHER PUBLICATIONS

CAS Registry Entry for Registry No. 910611-93-7, which entered STN on Oct. 18, 2006.*
International Search Report on PCT/GB2013/000208, date of mailing Jul. 18, 2013.

* cited by examiner

*Primary Examiner* — Matthew Coughlin
(74) *Attorney, Agent, or Firm* — Dority & Manning, P.A.

(57) ABSTRACT

Methods of producing OLED materials containing fluorene ring systems in which two alkyl substituents at the 9-position of fluorene ring are alkyl substituted through key intermediates generically represented by the formula: where X represents a substituent that increases the acidity of the hydrogen atoms on the adjoining methylene group (which is immediately adjacent the fluorene ring systems 9-position).

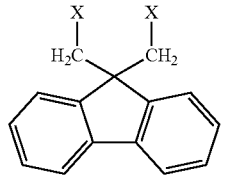

Formula 1

13 Claims, No Drawings

METHODS FOR PRODUCING ORGANIC LIGHT EMITTING DIODE (OLED) MATERIALS

This application is a 35 U.S.C. §371 national stage filing of International Application No. PCT/GB2013/000208, filed May 9, 2013, which claims priority to GB Patent Application No. 1208136.0, filed May 10, 2012. The entire contents of each of the aforementioned applications are incorporated herein by reference.

This invention relates to improved methods for producing Organic Light Emitting Diode (OLED) materials containing fluorene ring systems, such as those comprising spiro[cycloalkane-1,9-fluorene]s, spiro[bicycloalkane-9-fluorene]s, and 9,9-Di(1,1-dimethylalk-1-yl)fluorenes, and condensed ring systems incorporating these structures Organic Light Emitting Diode (OLED) materials containing fluorene ring systems in which two alkyl substituents at the 9-position of fluorene ring are alkyl substituted are desirable components for use in OLEDs because of their high oxidative stability. Previous methods of producing these materials were very low yielding.

The present invention provides methods by which these materials may be produced with higher yields.

The invention comprises methods of producing OLED materials containing fluorene ring systems in which two alkyl substituents at the 9-position of fluorene ring are alkyl substituted through key intermediates generically represented by the formula:

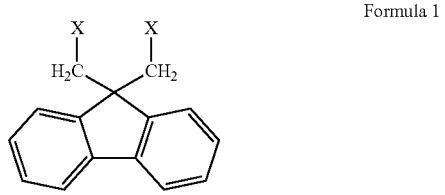

Formula 1 where X represents a substituent that increases the acidity of the hydrogen atoms on the adjoining methylene group (which is immediately adjacent the fluorene ring systems 9-position).

X may comprise an electron withdrawing group. Electron withdrawing groups that may be used include alkoxycarbonyl, cyano, 1,3-oxazol-2-yl, 1,3-thiazol-2-yl, 1,3-benzo[d]oxazol-2-yl, and 1,3-benzo[d]thiazol-2-yl.

The invention comprises a synthesis (Synthesis 1) for previously unknown compound, fluorene-9,9-diacetic acid, dimethyl ester, which corresponds to Formula 1 with X=methoxycarbonyl:

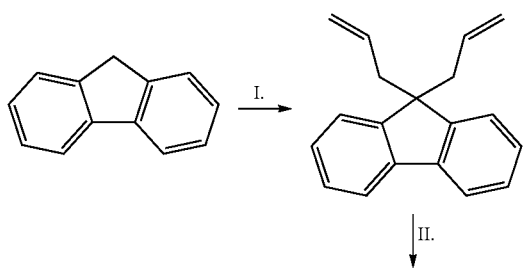

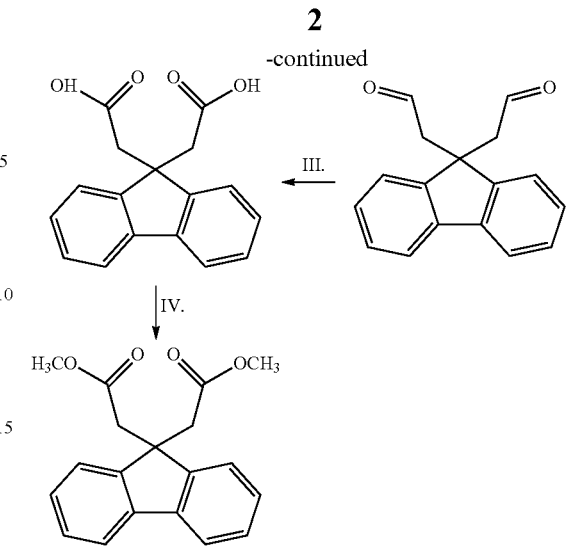

I. Allyl bromide, KOH, DMSO, 10° C.; II. RuCl$_3$xH$_2$O, NaIO$_4$, CH$_3$CN, H$_2$O; III. Jones Reagent; IV. CH$_3$OH, DMAP, DCC, CH$_2$CH$_2$.

An alternative pathway replaces step II with epoxidation with m-chloroperbenzoic acid followed by periodic acid oxidation to the dialdehyde. In either case the dialdehyde is, in fact, a polymeric hydrate similar to that formed by glutaraldehyde. Because of this the aldehyde and its imino or hydrazone derivatives are excluded from the list of candidate substituents X in Formula 1 since they do not, in fact, structurally exist.

The preferred X in Formula 1 is the 1,3-benzo[d]thiazol-2-yl radical. One reason for this is that the resulting compound (previously unknown), 2,2'(fluoren-9,9-diyldimethylene)bis-1,3-benzo[d]thiazole, is easily synthesised (Synthesis 2):

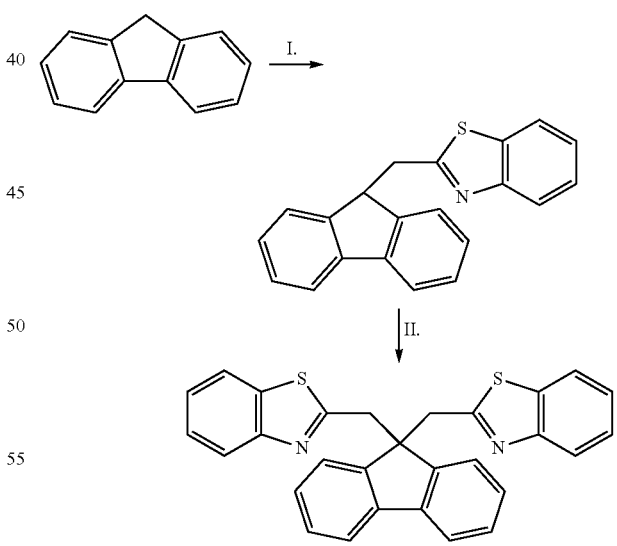

I. 1. lithium diisopropylamide, THF, 2. 2-bromomethyl-1,3-benzo[d]thiazole;
II. 1. lithium diisopropylamide, THF, 2. 2-bromomethyl-1,3-benzo[d]thiazole.

A further reason why this compound is the preferred intermediate is that the hydrogens on the methylenes adjacent to the groups X appear to have unusually low acidities for hydrogens located next to these activating groups, likely due to the effect of the fluorene ring. The nitrogenous bases such as lithium diisopropylamide (LDA) that are normally used to deprotonate such materials appear to only partially deprotonate the materials represented by FIG. 1 resulting in low yields. Sufficient deprotonation is only achieved by carbon-based bases like n-butyl lithium and t-butyl lithium. Thus only groups X which are stable to alkyl lithiums, e.g. 1,3-benzo[d]thiazol-2-yl, can yield complete deprotonation.

Following deprotonation the intermediate (Formula 1) is dialkylated to form a second intermediate. If monohaloalkanes are used for the alkylation, the second intermediate has the formula

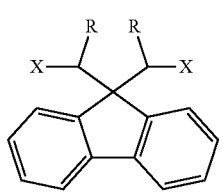

Formula 2

Here X has the same meaning as in Formula 1 and R is an alkyl group, most commonly n-alkyl, but branched chain alkyl groups may be used as well. 1-Bromo-n-alkanes are most commonly used in this synthetic step except that iodomethane is used if R is to be methyl. The Rs may be different. However, this introduces the problem of optical isomers in the final product. Aside from monohaloalkanes, alkanes substituted with other leaving groups such as methylsulphonates and p-toluenesulphonates may also be used.

If α,ω-dihaloalkanes are used spiro[cycloalkane-1,9-fluorenes] are the resulting second intermediates. In particular, dialkylation with 1-bromo-2-chloroethane and with 1-bromo-3-chloropropane result in spiro[cyclopentane-1,9-fluorene]s (Formula 3) and spiro[cyclohexane-1,9-fluorene]s (Formula 4) respectively.

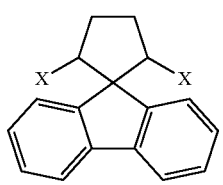

Formula 3

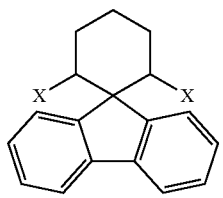

Formula 4

In addition, dialkylation of the deprotonated material of Formula 2 with 1-bromo-3-chloro-2,2-dimethylpropane and 3-bromomethyl-3chloromethyl-n-pentane result in 4,4-dimethylspiro[cyclohexane-1,9-fluorene]s (Formula 5) and 4,4-diethylspiro[cyclohexane-1,9-fluorene]s (Formula 6) respectively.

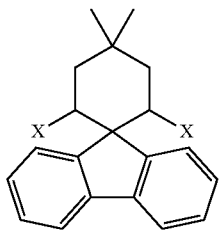

Formula 5

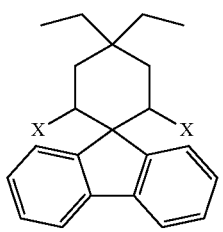

Formula 6

All of the spiro materials in FIGS. 3,4,5, and 6 may be generically represented by the formula

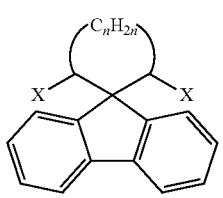

Formula 7

A particularly preferred compound of this type is

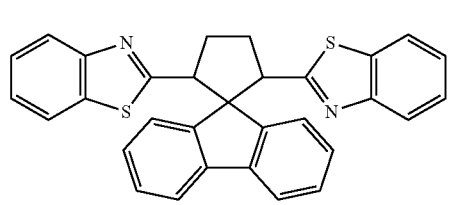

Formula 8

In the synthesis of the compound with Formula 8, the deprotonation and alkylation process may proceed in two steps:

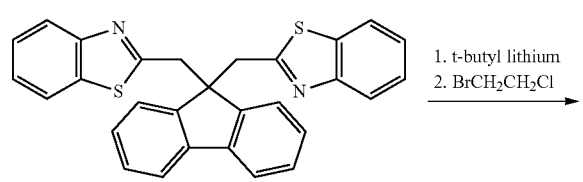

-continued

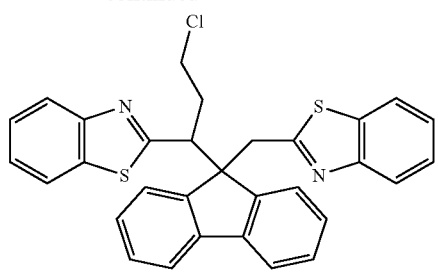

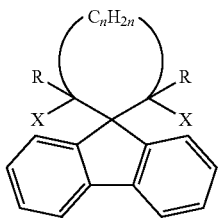

Formula 11

If the second intermediate has the structure shown in Formula 7, it may also be deprotonated with a strong base and then be dialkylated with a monohaloalkane or an α,ω-dihaloalkane. If it is dialkylated with a monohaloalkane the resulting product will have the structure shown in Formula 11. A preferred series of compounds of Formula 11 are

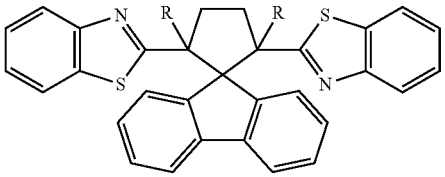

Formula 12

In the next step of this synthetic method, if the second intermediate has the structure shown in Formula 2, it may again be deprotonated with a strong base (e.g. t-butyl lithium) and then dialkylated with a monohaloalkane or an α,ω-dihaloalkane. If a monohaloalkane is used the resulting product will have the general formula If the dialkylation of the deprotonated material with structure shown in FIG. 7 is carried out using an α,ω-dihaloalkane, the resulting product will be a spiro[bicycloalkane-9-fluorene] of the general formula

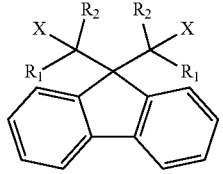

Formula 9

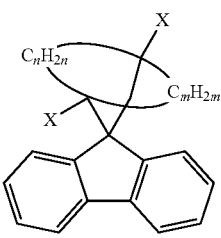

Formula 13

A preferred example of compounds with Formula 9 is

Preferred compounds with a structure shown in FIG. 13 are the material with n=2, m=2, and X=1,3-benzo[d]thiazol-2-yl,

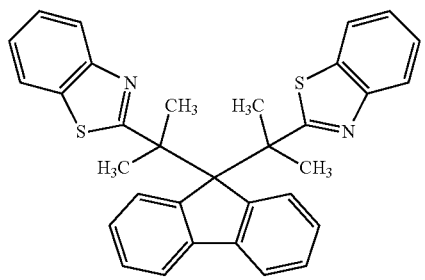

Formula 10

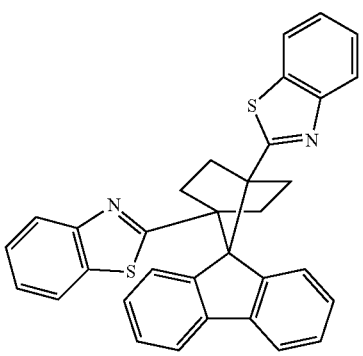

Formula 14

If the second intermediate of Formula 2 is deprotonated and then dialkylated with an α,ω-dihaloalkane the resulting product will have the general formula the material with n=3, m=2, and X=1,3-benzo[d]thiazol-2-yl, and

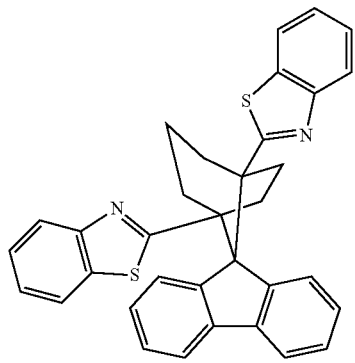

Formula 15 the material with n=3, m=3, and X=1,3-benzo[d]thiazol-2-yl.

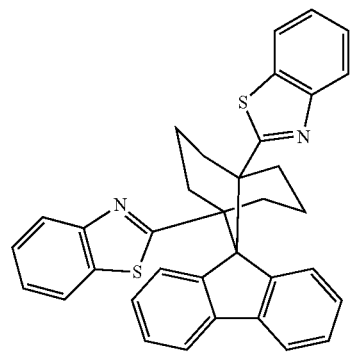

Formula 16

Electron withdrawing groups that may be used in compounds with formulae 2 and 7 so as to allow further deprotonation and alkylation include 1,3-thiazol-2-yl, 1,3-benzo[d]oxazol-2-yl, and 1,3-benzo[d]thiazol-2-yl and N-alkylimino.

The 1,3-oxazol-2-yl, 1,3-thiazol-2-yl, 1,3-benzo[d]oxazol-2-yl, and 1,3-benzo[d]thiazol-2-yl functions in compounds of formulae 7, 9, 11, and 13 may be converted into aldehyde functions by a previously known series of steps, for instance,

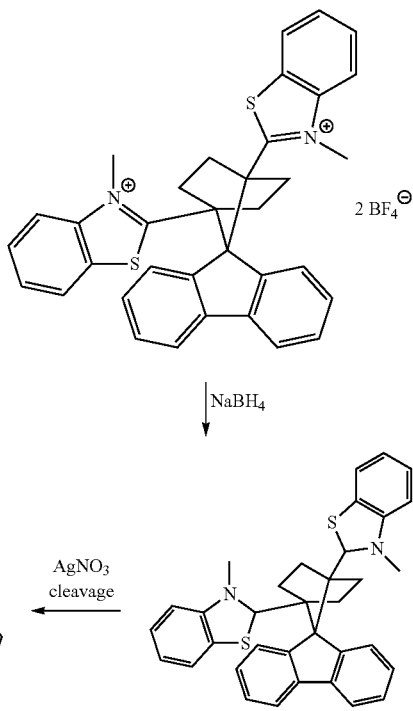

The intermediates of Formula 1 may be substituted at any of the positions on the fluorene ring system. In particular, the fluorene may fused to further aromatic rings, e.g.

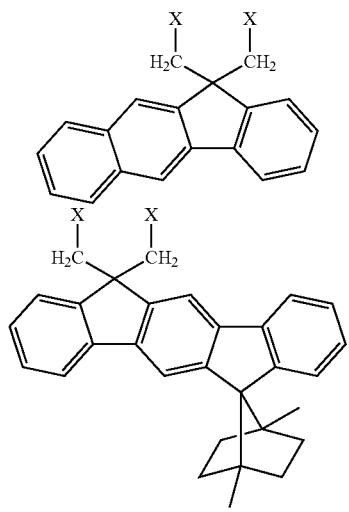

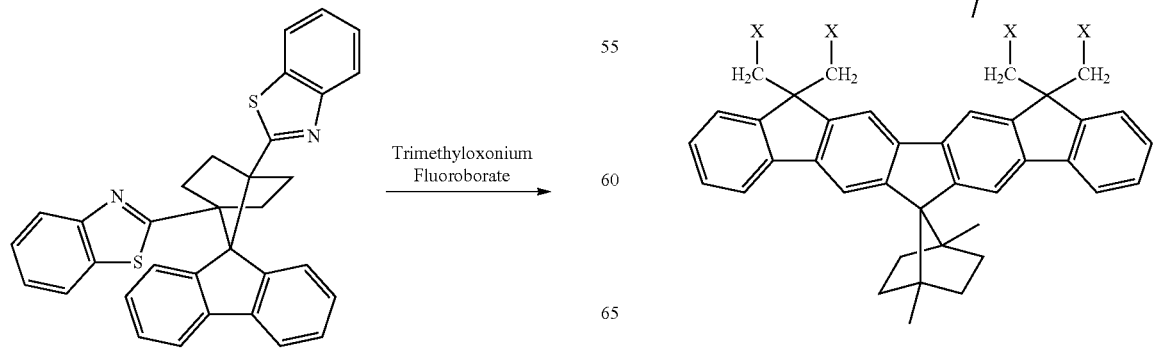

Compounds with formulae 2,7,9,11, and 13 may be similarly substituted or fused.

A further preferred synthetic variation of this method (Synthesis 3) utilises a variant of the intermediate with Formula 2 in which R has the formula $—(CH_2)_nY$

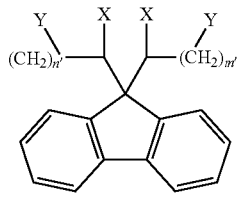

In this synthesis Y is converted by a series of synthetic steps to a second intermediate with Formula 2 with $R'=—(CH_2)_mY'$

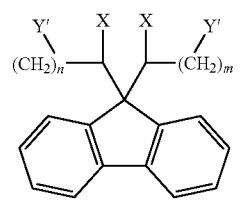

wherein Y' is a leaving group such as iodo, bromo, chloro, p-toluenesulfonato, methanesufonato, trifluoromethanesulfonato, etc.

Treatment of this second intermediate with a strong base converts the material to a product with Formula 13:

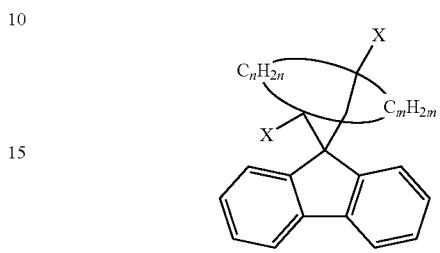

A first example of this synthesis is:

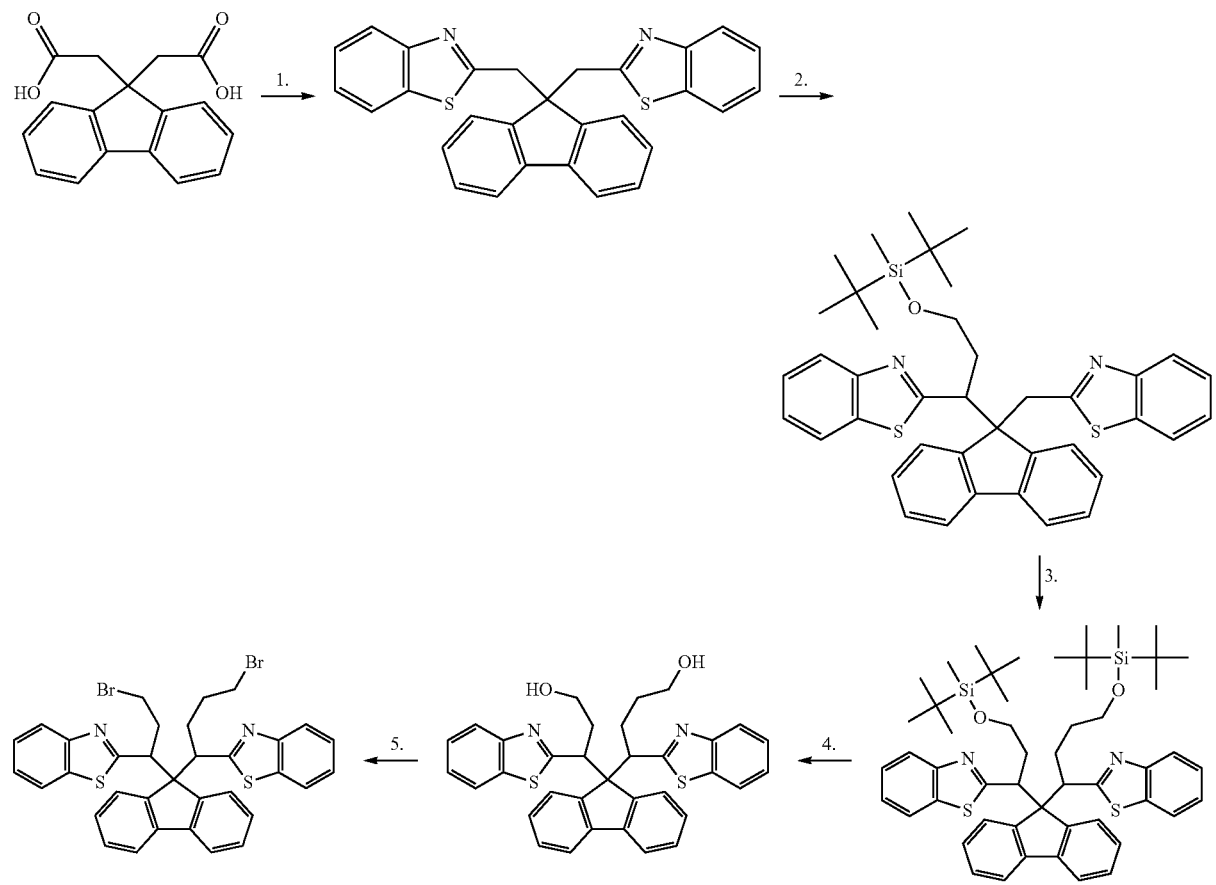

1. 2-Aminobenzenethiol, polyphosphoric acid, 190 degrees C for 4 hours;
2. a. t-Butyl lithium in dry THF at -78 degrees for 3 hours, b. 1-Bromo-2-(Di-t-butylmethylsilyloxy)ethane at -78 degrees C for 0.5 hours;
3. a. t-Butyl lithium in dry THF at -78 degrees for 3 hours, b. 1-Bromo-3-(Di-t-butylmethylsilyloxy)propane at -78 degrees C for 0.5 hours;
4. 5 Equivalents of tetrabutylammonium fluoride in THF at RT overnight.
5. Triphenylphosphine dibromide in DMF at 0 degrees C then allow to warm to RT overnight.

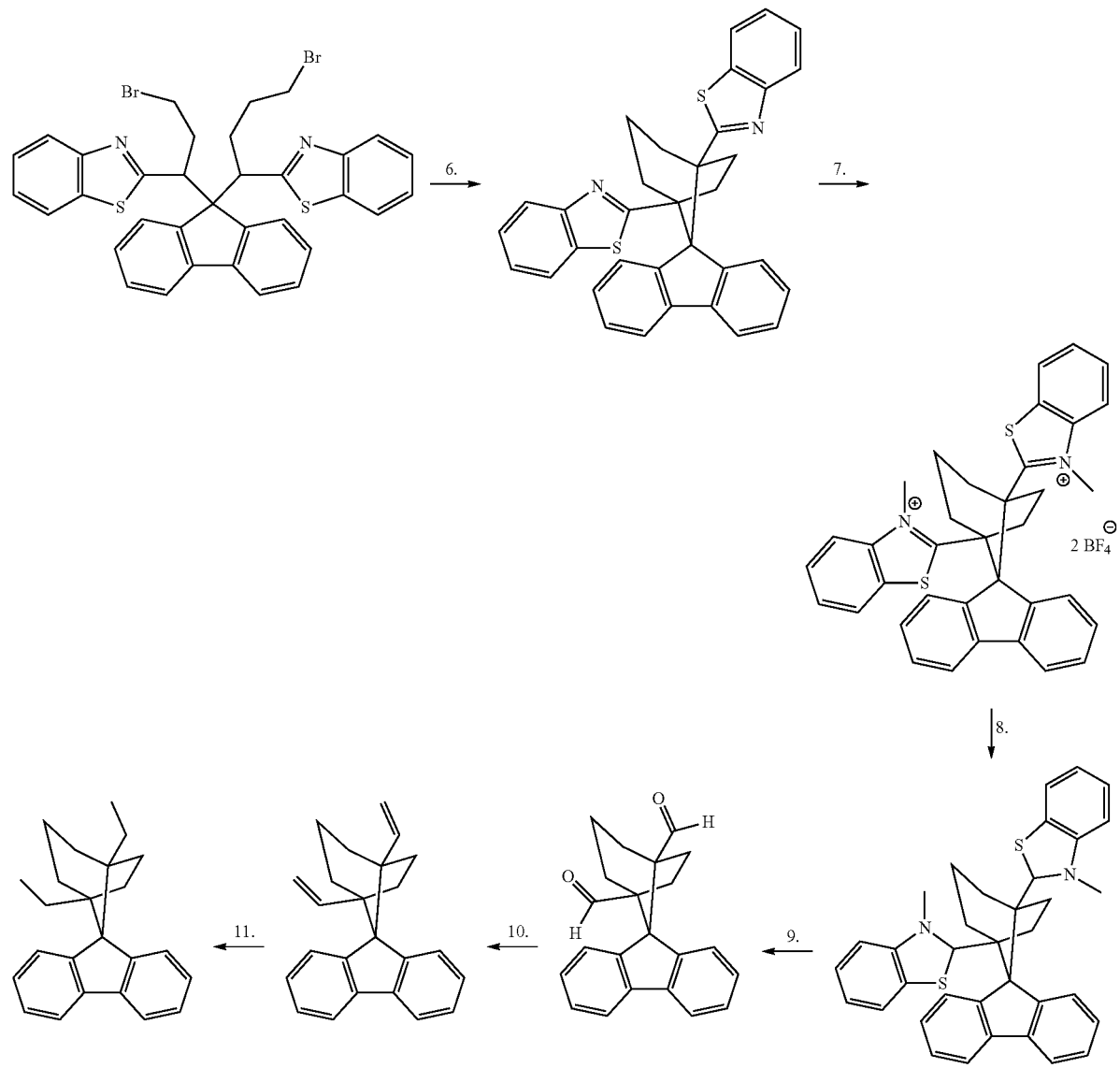

6. t-Butyl lithium in dry THF at -78 degrees C and then let warm to RT overnight.
7. (CH₃)₃O⁻ BF₄⁻ in dry dichloromethane at RT for 24 hours
8. NaBH₄ in ehtanol at RT with vigorous stirring for 2 hours
9. a. AgNO₃ and pH 7 buffer in water/CH₃CN at RT for 3 hours, b. triethylamine at 45 to 50 degrees C for 2 hours.
10. Methylenetriphenylphosphorane in dry ether refluxed for 12 hours.
11. 3 atm. H2 with 10% Pd on carbon in tetrahydrofuran for five hours in a Parr shaker.

A second example synthesis is:

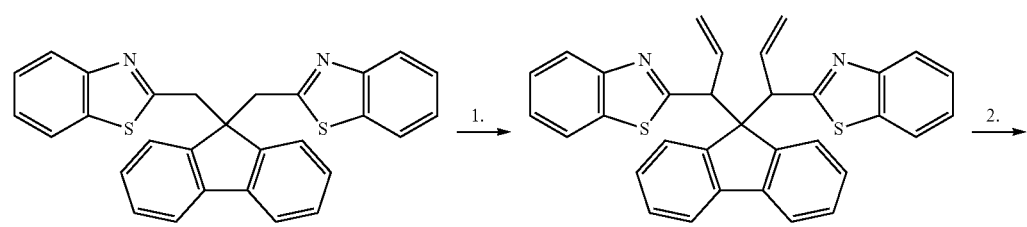

-continued

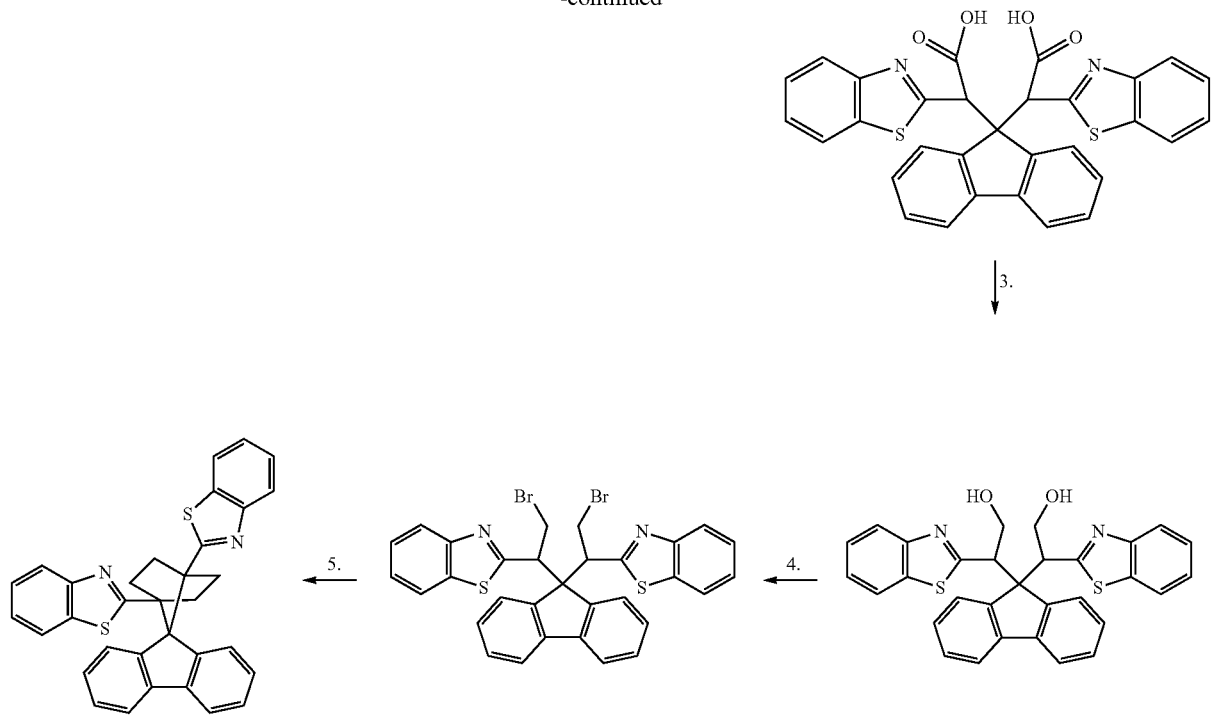

1. a. t-Butyl lithium in dry THF at -78 degrees for 3 hours, b. Allyl bromide at -78 degrees C for 0.5 hours;
2. Sodium metaperiodate, catalytic potassium permanganate, and sodium carbonate in pyridine/water solvent at room temperature.
3. LiAlH$_4$ in tetrahydrofuran at 0 degrees C followed by 2 hours reflux.
4. Triphenylphosphine dibromide in DMF at 0 degrees C then allow to warm to RT overnight.
5. t-Butyl lithium in dry THF at -78 degrees C and then let warm to RT overnight.

A third example of the synthesis is:

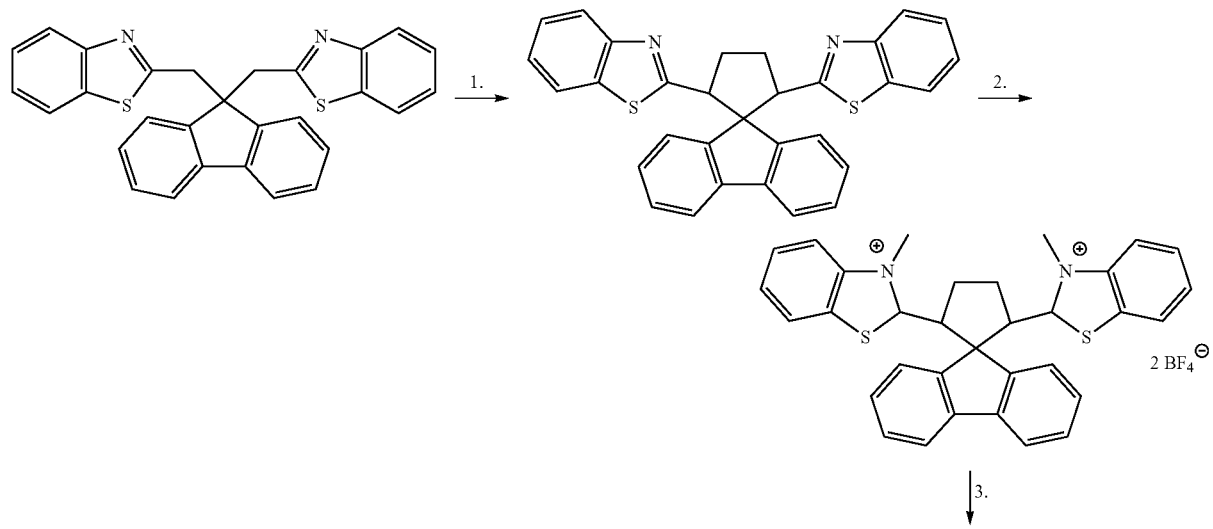

-continued

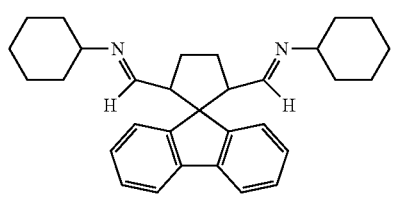 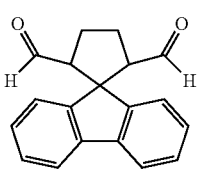

Unisolated
Intermediate 1. a. t-Butyl lithium in dry THF at -78 degrees for 3 hours. b. 1-Bromo-2-chloroethane at -78 degrees C for 0.5 hours then allow to warm to RT overnight;
2. (CH₃)₃O⁺ BR₄⁻ in dry dichloromethane at RT for 24 hours;
3. NaBH₄ in ethanol at RT with vigorous stirring for 2 hours;
4. a. AgNO₃ and pH 7 buffer in water/CH₃CN at RT for 3 hours, b. triethylamine at 45 to 50 degrees C for 2 hours;
5. Cyclohexylamine an benzene solvent. azeotrope for 6 hours.

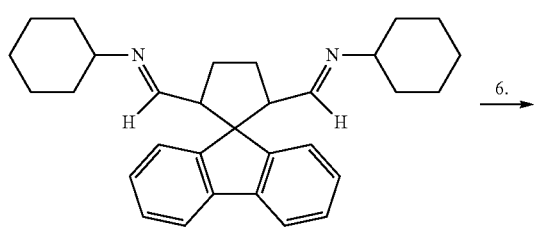

Unisolated
Intermediate

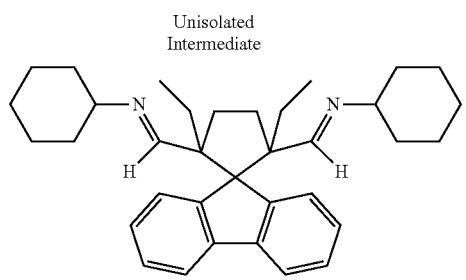

Unisolated
Intermediate

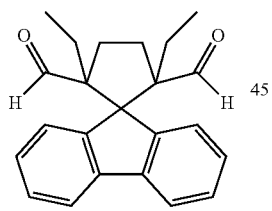

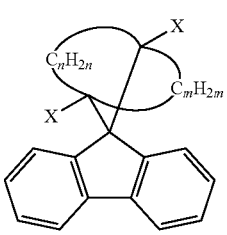

6. a. Lithium diisopropylamide and hexamethylphosphoramide in dry THF at 0 degrees for 3 hours, b. 1-Iodobutaneat at 0 degrees for 15 min. and then allow to warm to RT overnight;
7. 1 Molar oxalic acid at RT for 2 hours;
8. Methylenetriphenylphosphorane in dry ether refluxed for 12 hours;
9. 3 atm. H₂ with 10% Pd on carbon in tetrahydrofuran for five hours in a Parr shaker.

The invention claimed is:

1. A method of producing fluorene OLED materials, the method comprising the steps of:
   (a) deprotonation and alkylation of a compound of Formula 1:

Formula 1

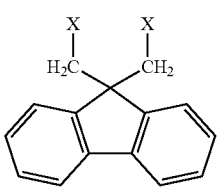

to produce a compound of Formula 7:

Formula 7

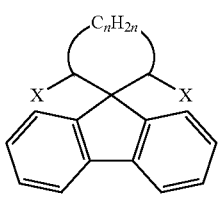

(b) deprotonation and alkylation of the compound of Formula 7 to produce an OLED material of Formula 13:

Formula 13

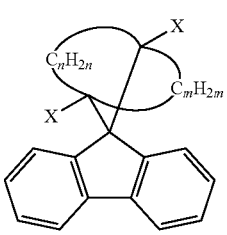

where X represents 1.3-benzo[d]thiazol-2-yl,
wherein the deprotonation is with an alkyl lithium base,
wherein the alkylation is with an α,ω-dihaloalkane, and
wherein n and m are independently of one another 2 or 3.

2. The method of claim 1, wherein the alkyl lithium base is n-butyl lithium.

3. The method of claim 1, wherein the alkyl lithium base is t-butyl lithium.

4. The method of claim 1, wherein the α,ω-dihaloalkane is 1-bromo-2-chloroethane.

5. The method of claim 2, wherein the α,ω-dihaloalkane is 1-bromo-2-chloroethane.

6. The method of claim 3, wherein the α,ω-dihaloalkane is 1-bromo-2-chloroethane.

7. The method of claim 1, wherein the α,ω-dihaloalkane is 1-bromo-3-chloropropane.

8. The method of claim 2, wherein the α,ω-dihaloalkane is 1-bromo-3-chloropropane.

9. The method of claim 3, wherein the α,ω-dihaloalkane is 1-bromo-3-chloropropane.

10. The method of claim 1, wherein n is 2 and m is 2.

11. The method of claim 1, wherein n is 3 and m is 2.

12. The method of claim 1, wherein n is 3 and m is 3.

13. A compound 2,2'(fluoren-9,9-diyldimethylene)bis-1,3-benzo[d]thiazole having the formula

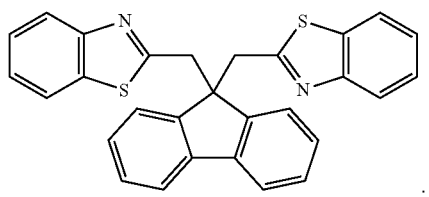 [SMILES: c1ccc2c(c1)-c1ccccc1C2(Cc1nc2ccccc2s1)Cc1nc2ccccc2s1]

* * * * *